(12) United States Patent
Hunter et al.

(10) Patent No.: US 6,642,361 B2
(45) Date of Patent: Nov. 4, 2003

(54) **ISOLATED COCOON SILK PROTEIN FROM *SIMULIUM VITTATUM* AND NUCLEIC ACIDS ENCODING SUCH PROTEIN**

(76) Inventors: Fiona F. Hunter, 500 Glenridge Avenue, St. Catherines, Ontario (CA), L2S 3A1; Michael J. Bidochka, 500 Glenridge Avenue, St. Catherines, Ontario (CA), L2S 3A1

( * ) Notice: Subject to any disclaimer, the term of this patent is extended or adjusted under 35 U.S.C. 154(b) by 0 days.

(21) Appl. No.: 09/894,916

(22) Filed: Jun. 28, 2001

(65) Prior Publication Data

US 2003/0032089 A1 Feb. 13, 2003

Related U.S. Application Data

(60) Provisional application No. 60/214,992, filed on Jun. 29, 2000.

(51) Int. Cl.⁷ ................................................ A61K 38/17
(52) U.S. Cl. ...................................... 530/353; 530/300
(58) Field of Search .................... 530/350, 353, 530/334, 412, 422, 369, 402; 435/18; 8/128.1

(56) References Cited

U.S. PATENT DOCUMENTS 5,245,012 A    9/1993  Lombardi et al.
5,728,810 A    3/1998  Lewis et al.
5,733,771 A  * 3/1998  Lewis et al. ............. 435/252.3

FOREIGN PATENT DOCUMENTS

WO     WO 97/08315    *  3/1997  ........... C12N/15/12

OTHER PUBLICATIONS

Tokutake, S. (1980) Isolation of the smallest component of silk protein. Biochem. J. vol. 187, pp. 413–417.*

* cited by examiner

*Primary Examiner*—Karen Cochrane Carlson
*Assistant Examiner*—Samuel Wei Liu
(74) *Attorney, Agent, or Firm*—Goodwin Procter LLP

(57) ABSTRACT

An isolated nucleic acid molecule encoding the cocoon silk protein from the black fly, *Simulium vittatum*. Also provided are the amino acid sequence derived from the cocoon silk, primers used to screen cDNA libraries to promote the building of a complimentary strand of DNA encoding the cocoon silk protein, a transformed microorganism containing cDNA which codes for cocoon silk protein, the amino acid sequence translated from the isolated gene of the cocoon silk (deduced from nucleotide sequence), primers for constructing a segment of recombinant DNA.

4 Claims, No Drawings

SEQUENCE LISTING

<160> NUMBER OF SEQ ID NOS: 7

<210> SEQ ID NO 1
<211> LENGTH: 20
<212> TYPE: PRT
<213> ORGANISM: Simulium vittatum

<400> SEQUENCE: 1

Gly Val Ala Pro Lys Lys Tyr Arg Lys Gly His Tyr Val Gly Gly Tyr
1               5                   10                  15

Gly Lys Lys Tyr
            20

```
<210> SEQ ID NO 2
<211> LENGTH: 60
<212> TYPE: DNA
<213> ORGANISM: Simulium vittatum
<220> FEATURE:
<221> NAME/KEY: misc_feature
<222> LOCATION: (1)..(60)
<223> OTHER INFORMATION: n can be any of A, T, G or C

<400> SEQUENCE: 2
ggngtngcnc cnaanaanta ncgnaanggn cantangtng gnggntangg naanaantan    60

<210> SEQ ID NO 3
<211> LENGTH: 45
<212> TYPE: DNA
<213> ORGANISM: Simulium vittatum
<220> FEATURE:
<221> NAME/KEY: misc_feature
<222> LOCATION: (44)..(45)
<223> OTHER INFORMATION: n can be any of A, T, G or C

<400> SEQUENCE: 3
ttttgtacaa gctttttttt tttttttttt tttttttttt tttnn                    45

<210> SEQ ID NO 4
<211> LENGTH: 23
<212> TYPE: DNA
<213> ORGANISM: T7 primer

<400> SEQUENCE: 4
taatacgact cactataggg cga                                            23

<210> SEQ ID NO 5
<211> LENGTH: 23
<212> TYPE: DNA
<213> ORGANISM: SP6 primer

<400> SEQUENCE: 5
atttaggtga cactatagaa tac                                            23

<210> SEQ ID NO 6
<211> LENGTH: 831
<212> TYPE: DNA
<213> ORGANISM: Simulium vittatum

<400> SEQUENCE: 6
agctctccca tatggtcgac ctgcaggcgg ccgcactagt gattggagtt gctccaaaga    60
agtaccgcaa gggacactat gtcgggggtt acgggaagaa gtatcgtatt tttgacagca   120
attgtgctat gaacaacgcc aactgtcaga atccaaacga atccgccttc gccgaagttg   180
atttcacgct gtgcaatgat atcaaatgtc ctaggaaatg cgataaaaaa ctagacccgg   240
tttgtgcttt tgatgggaaa acgtacagac aatttaacaa caaatgtctg ctgcaagaat   300
tcaatgattg cgatcaaaat gtgtttcaat atttcaacgc tgtgactaac aaaaaaatgt   360
gcgtggttga gaagccaaaa tgcccgacca tttgtccagc aatttatgct cccgtttgtg   420
gtcgaaatgc caagggggat tacaaaagtt ttgcgagtga atgcaaccaa tccgcattca   480
actgcttgat ttctaagaat caatatacgg gcaagtatga tttgagtttt tgcgacatcg   540
agttccctta agcatgacgt tgtaacgttt tttctctgga tgtgcaaaac ataaattaca   600
agcactggat tgaatggtgt tttattaaat ttccttgtga cctttttttcc attattcttt   660 ccggccttta acaagtaatc aatattgata tcggtcgttt ttgtaaagat tttttttcag   720
```

-continued

```
taaaaatatc catctcattt tcacaaaaaa aaaaaaaaaa aaaaaaaaaa aaaaagcttg    780
tacaaaaaat cccgcggcca tggcggccgg gagcatgcga cgtcgggccc a             831
```

<210> SEQ ID NO 7
<211> LENGTH: 168
<212> TYPE: PRT
<213> ORGANISM: Simulium vittatum

<400> SEQUENCE: 7

```
Gly Val Ala Pro Lys Lys Tyr Arg Lys Gly His Tyr Val Gly Gly Tyr
1               5                   10                  15

Gly Lys Lys Tyr Arg Ile Phe Asp Ser Asn Cys Ala Met Asn Asn Ala
            20                  25                  30

Asn Cys Gln Asn Pro Asn Glu Ser Ala Phe Ala Glu Val Asp Phe Thr
        35                  40                  45

Leu Cys Asn Asp Ile Lys Cys Pro Arg Lys Cys Asp Lys Lys Leu Asp
    50                  55                  60

Pro Val Cys Ala Phe Asp Gly Lys Thr Tyr Arg Gln Phe Asn Asn Lys
65                  70                  75                  80

Cys Leu Leu Gln Glu Phe Asn Asp Cys Asp Gln Asn Val Phe Gln Tyr
                85                  90                  95

Phe Asn Ala Val Thr Asn Lys Lys Met Cys Val Val Glu Lys Pro Lys
            100                 105                 110

Cys Pro Thr Ile Cys Pro Ala Ile Tyr Ala Pro Val Cys Gly Arg Asn
        115                 120                 125

Ala Lys Gly Asp Tyr Lys Ser Phe Ala Ser Glu Cys Asn Gln Ser Ala
    130                 135                 140

Phe Asn Cys Leu Asn Ser Lys Asn Gln Tyr Thr Gly Lys Tyr Asp Leu
145                 150                 155                 160

Ser Phe Cys Asp Ile Glu Phe Pro
                165
```

ISOLATED COCOON SILK PROTEIN FROM *SIMULIUM VITTATUM* AND NUCLEIC ACIDS ENCODING SUCH PROTEIN

This application claims priority from U.S. Provisional Application No. 60/214,992, filed Jun. 29, 2000 which is herein incorporated by reference in its entirety.

The sequence listing information submitted on computer readable form is identical to the written sequence listing contemporaneously submitted on paper, and includes no new matter.

FIELD OF THE INVENTION

The present invention relates to the cocoon silk protein isolated from the black fly, *Simulium vittatum.*

BACKGROUND OF THE INVENTION

Silk is a natural, protein filament fiber. Several types of natural silk that are known to date are excreted by invertebrates such as those that belong to two classes of the phylum Arthropoda: Insecta and Arachnida. Silk producing insects include silk worms, black flies, wasps, and lacewing flies.

Some arthropods' silk have now been cloned. For example, Lewis, R. V. et al. (U.S. Pat. No. 5,728,810) teach the preparation of spider silk protein by recombinant DNA techniques. Lewis, R. V., et al. (U.S. Pat. No. 5,733,771) teach a cDNA encoding minor ampulate silk proteins. Lombardi, S. J. et al. (U.S. Pat. No. 5,245,012) teach a recombinant spider silk protein which can be obtained in a commercially useful form by the cloning of host cells encoding such protein.

Another silk producing arthropod, the black fly, evolved to produce a very durable silk filament. Silk is produced by the black fly "larva" which forms a cocoon. The larva and pupae are aquatic but are confined to running waters where they attach themselves to firm substrates. The black fly's silk filament is able to withstand the exposure to water flow in order to keep the pupa inside the cocoon intact. Another remarkable property of the Simuliidae silk is its ability to maintain its adhesive characteristic while submerged in water. These properties are very attractive in terms of possible application of the black fly silk as a biomaterial.

The above prior art references are incorporated herein by reference.

The prior art does not teach the isolation of a nucleic acid molecule coding for the silk protein from black flies. Further, the prior art does not teach the expression of such silk protein using recombinant DNA techniques.

SUMMARY OF THE INVENTION

In one embodiment, the present invention provides an isolated polypeptide molecule having an amino acid sequence of SEQ ID NO: 1. In a further embodiment, the present invention provides an isolated nucleic acid molecule coding for such polypeptide. In another embodiment, the present invention provides the nucleic acid molecule comprising the nucleotide sequence of SEQ ID NO: 6. In a further embodiment, the present invention provides a polypeptide molecule having an amino acid sequence of SEQ ID NO: 7 and expressed by such nucleic acid molecule. In yet another embodiment, the present invention provides an isolated nucleic acid molecule coding for such polypeptide. In addition, the present invention provides a cloning vector comprising the nucleotide sequence of SEQ ID NO: 6 and a host cell transformed with such vector. In a further embodiment, the present invention provides a fiber formed from polypeptide of SEQ ID NO: 7. In yet another embodiment, the present invention provides a method of isolating cocoon silk protein comprising the steps of: a) boiling a cocoon in a sample reducing buffer to remove SDS (sodium dodecyl sulfate)-soluble proteins, b) centrifuging the sample, c) withdrawing supernatant, adding formic acid to the pellet and incubating the sample in order to solubilize SDS-insoluble proteins, d) freezing and lyophilizing the sample in order to freeze-dry the sample, e) re-suspending the dried sample in a buffer to protect proteins against potential residual proteolytic activity for subsequent analysis using SDS-PAGE (polyacrylamide gel electrophoresis).

DESCRIPTION OF THE PREFERRED EMBODIMENTS

In a preferred embodiment, the present invention provides an isolated nucleic acid molecule encoding the silk protein of black fly cocoons. The invention also provides amino acid molecules expressed by such nucleic acid as well as cells transformed with such nucleic acid molecule. Also provided are primers for screening DNA libraries for the DNA encoding the subject silk protein.

Methods and Results of Research

1. Method of Isolating and Purifying Cocoon Silk Protein from *Simulium vittatum*

The following method was developed for isolating and purifying cocoon silk protein from the black fly, *Simulium vittatum*. In the preferred embodiment, the method comprises the following procedure. A single cocoon from *S. vittatum* was boiled in 500 $\mu$l sample reducing buffer for one minute and then centrifuged for one minute at 13,000 rpm. Boiling in sample reducing buffer removes any SDS-soluble proteins. The composition of sample reducing buffer is as follows:

1 mL 0.5M Tris-HCl, pH 6.8

0.8 mL glycerol 1.6 mL

10% SDS (sodium dodecyl sulfate)

0.4 mL 2β mercaptoethanol 0.2 mL 0.5% bromophenol blue 4 mL $H_2O$

The supernatant was then removed and the sample was washed 4 times with $dH_2O$ by spinning the sample down and pouring off water between washes. Then the pellet was re-suspended in 500 $\mu$l of 90% formic acid and the sample was incubated in a shaker at 22° C. for 1 hour in order to solubilize the SDS-insoluble proteins. The sample was then frozen and lyophilized in order to be freeze-dried. Then the sample (formic acid and cocoon) was transferred to a 50 mL centrifuge tube and the volume was increased to 50 mL by the addition of $dH_2O$. This centrifuge tube was then frozen in a −70° C. freezer and the sample was lyophilized. After that, the sample was re-suspended in 400 $\mu$l of TEPI. TEPI buffer contains:

10 mM Tris-HCl, pH 8.0

1 mM EDTA (ethylenediaminetetraacidic acid)

1 $\mu$M phenylmethylsulfonylfluoride (PMSF)

100 $\mu$M iodoacetamide

Re-suspension in TEPI protected proteins against potential residual proteolytic activity for subsequent analysis using SDS polyacrylamide gel electrophoresis (SDS-PAGE). The sample was then run on a SDS-polyacrylamide gel in duplicate using standard procedures outlined in Laemmli (Cleavage of Structural Proteins During the Assembly of the Head of Bacteriophage T4, Nature, 1970, 227:680–685, the content of which we incorporate herein by reference). One gel was silver stained and the other was transferred to a poly-vinylidene-difluoride (PVDF) membrane which was stained with Ponceau stain. The band on the gel that corresponded to the cocoon silk protein of S. vittatum was excised using a razor blade and sent to the Centre de Recherche du CHUL (Quebec, Canada) for N-terminal amino acid sequencing.

2. N-terminal Amino Acid Sequence for Black Fly Cocoon Silk

The N-terminal amino acid sequencing of the silk protein isolated above revealed the following sequence:
GVAPKKYRKGHYVGGYGKKY SEQ ID NO: 1

3. cDNA Construction

In the preferred embodiment, cDNA was constructed as follows. Salivary glands were dissected from 10 S. vittatum larvae and placed into an RNAse free Eppendorf tubule, on ice. After that, 1 mL of TRIZOL™ reagent (Life Technologies Inc.) was added. Total RNA was recovered using manufacturer's instructions.

Poly $A^+$ mRNA was then isolated from the total RNA using Qiagen's Oligotex™ mRNA Kit. Oligotex provides a hybridization carrier on which nucleic acids containing polyadenylic acid sequences can be simply and efficiently immobilized and easily recovered. Briefly, the Oligotex procedure for isolation and purification of poly $A^+$ mRNA takes advantage of the fact that most eukaryotic mRNAs end in a homopolymer of 20–250 adenosine nucleotides, known as the poly A tail. The poly A tail is added to the RNA transcript in the nucleus following transcription. In contrast, structural RNAs are not polyadenylated. Nuclear polyadenylation of mRNAs performed by the eukaryotic cell provides molecular biologists with a useful tool for separation or selective isolation of poly $A^+$ mRNAs from total cellular RNA. Separation of poly a $A^+$ mRNAs from rRNA and tRNA can be achieved by hybridizing the polyadenylated tails of mRNA molecules to oligo dT primers which are coupled to a solid phase matrix. RNA species lacking poly A (rRNA and tRNA) fail to bind to oligo dT and are removed. Since high salt conditions are necessary to allow hybridization, the poly $A^+$ mRNA can subsequently be released by lowering the ionic strength and destabilizing the dT:A hybrids.

Upon the poly $A^+$ mRNA isolation, a cDNA library was constructed using RT-PCR (reverse transcription—polymerase chain reaction) following the Omniscript Protocol for Reverse Transcription (Omniscript Reverse Transcriptase Handbook, 1999, the content of which we incorporate herein by reference). Reverse transcriptase is a multifunctional enzyme with several distinct enzymatic activities, two of which, an RNA-dependant DNA polymerase and a hybrid-dependent exoribonuclease (RNase H), are utilized for reverse transcription in vitro to produce single-stranded cDNA with RNA as a starting template. The RNA-dependent DNA-polymerase activity (reverse transcription) transcribes cDNA from an RNA template which allows synthesis of cDNA for subsequent PCR. An exoribonuclease activity (RNase H) of Omnicript Reverse Transcriptase specifically degrades only the RNA in RNA:DNA hybrids. This Omniscript RNAse H activity affects RNA that is hybridized to cDNA and also improves the sensitivity of subsequent PCR.

The reverse-transcription (RT) reaction conditions were as follows:

| | |
|---|---:|
| 10X Buffer RT | 2.0 μL |
| dNTP mix (5 mM each dNTP) | 2.0 μL |
| Oligo-dT primer (SEQ ID NO: 3) 10 μM | 2.0 μL |
| RNase inhibitor (10 units/μL) | 1.0 μL |
| Omniscript Reverse Transcriptase (4 units/μL) | 1.0 μL |
| RNase-free water | 9.0 μL |
| Template poly A + RNA (~25 ng/μL) | 3.0 μL |
| Total | 20 μL |

4. 60-Nucleotide Primer Used to Screen cDNA Library for Cocoon Silk Protein Transcript Two primers may be preferably used to promote the building of a new strand of DNA encoding the cocoon silk protein after DNA strands were separated by heating during the PCR process.

Primer #1, the cocoon silk protein primer, was a degenerate primer of the following structure:

5' end

```
GGN GTN GCN CCN AAN AAN TAN CGN AAN GGN CAN TAN GTN    SEQ ID NO: 2
GGN GGN TAN GGN AAN AAN TAN
```

Primer #2 was a poly-T primer of the following structure:

5'-TTTTGTACAAGCTT$_{30}$N$_2$-3',                SEQ ID NO: 3 where N can be any of A, T, G or C.

where N can be any of A, T, G or C.

The conditions of the polymerase chain reaction were as follows:

1. The PCR Mixture, Using the Qiagen kit, Catalogue No. 201203, Consisted of

| | |
|---|---:|
| Q-solution 10X | 4 μL |
| 10X PCR Buffer (with 15 Mm MgCl$_2$) | 2 μL |
| dNTPs solution containing 10 mM of each dNTP | 2 μL |
| MgCl$_2$ 25 mM | 1 μL |
| 10 μM Oligo-dT primer (SEQ ID NO: 3) | 1 μL |
| 85 pmoles/μL cocoon silk protein primer (SEQ ID NO: 2) | 0.4 μL |
| Taq polymerase (5 units/μL) | 0.2 μL |
| Template (finished RT product, ~25 ng/μL) | 4 μL |
| dH$_2$O | 5.4 μL |
| Total | 20 μL |

For PCR following RT, Omniscript recommends no more than ⅕ of the total reaction volume should be derived from the finished RT product. The maximum recommended was used, i.e. 4 μL of 20 μL.

2. The Thermocycler Program was as Follows

| | |
|---|---|
| 1) 95° C. | 15 min |
| 2) 94° C. | 2 min 30 sec |
| 3) 55° C. | 3 min |
| 4) 72° C. | 2 min 30 sec |
| 5) 72° C. | 5 min final extension |

Steps 2–4 were run for 45 cycles. The sample was then run on an ethidium bromide gel and a single band <750 bp was visualized.

5. Ligation of RT-PCR Product Using pGEM-T™ Vector System from Promega

The RT-PCR product of step 4 was then ligated preferably using pGEM-T™ Easy Vector System from Promega (Cat. No. A3600). The resultant DNA from the RT-PCR reaction was purified using a GFX™ PCR DNA and Gel Band Purification kit (Amersham Pharmacia Biotech, Cat. No. 27-9602-01) according to manufacturer's instructions and eluted in 40 μL dH$_2$O. The above purification removes salts, enzyme, unincorporated nucleotides and promoters from PCR products. The resulting concentration of RT-PCR DNA was approximately 20 ng/μL. This purified RT-PCR DNA, approximately 0.7 kb in length, was then used as an insert for ligation into a pGEM-T™ Vector plasmid following the steps in "The Experienced User's Protocol for Promega pGEM-T™ Vector Systems", the content of which is incorporated herein by reference. The ligation mixture used was as follows:

| | |
|---|---|
| 2X Rapid Ligation Buffer, T4 DNA ligase | 5 μL |
| pGEM-T vector (50 ng) | 1 μL |
| purified RT-PCR DNA (20 ng/μL) | 3 μL |
| T4 DNA ligase (3 Weiss Unit/μL) | 1 μL |
| Total | 10 μL |

6. Transformation of E. coli XL1 Blue Cells

E. coli XL1 Blue cells were transformed with the ligation mixture of step 5 as follows. E. coli XL1 Blue cells (Stratagene) were made competent, i.e. those cells were treated to enhance their ability to take up DNA. Protocol to make cells competent was modified from Sambrook, J., Fritsch, E. F., and Maniatis, T., 1989, Molecular Cloning: A Laboratory Manual, 2$^{nd}$ Edition, Cold Spring Harbor Laboratory Press, the content of which we incorporate herein by reference. The actual procedure for making E. coli XL1 Blue cells (Stratagene) competent was as follows.

E. coli strain XL1-Blue cells were grown for 18 hours in 5 ml of LB broth at 37° C. and 250 rpm shaking (LB is Luria-Burtani Medium (pH 7.0) containing 2 g bactotryptone, 1 g bacto-yeast extract, 2 g NaCl in 200 mL dH$_2$O). Then, 200 μl of the above mixture with E. coli cells was transferred into 50 ml of new LB broth and grown for 3 hours at 37° C. and 250 rpm shaking. After that, the mixture was centrifuged at 7.5K rpm for 3 minutes and supernatant was discarded. The cells were then re-suspended in 5 ml of Buffer A. The composition of the Buffer A was as follows: 100 mM NaCl, 5 mM MgCl$_2$, 5 mM Tris-HCl, pH 7.5. Re-suspended E. coli cells were incubated on ice for 10 minutes and centrifuged at 7.5K rpm for 3 minutes. After that, a supernatant was discarded and a residue re-suspended in 5 ml of Buffer B. The composition of the Buffer B was as follows: 100 mM CaCl$_2$, 5 mM MgCl$_2$, 5 mM Tris-HCl, pH 7.5. The resulting mixture with E. coli cells was incubated on ice for 30 minutes and the cells became competent. 10 μL of the ligation mixture (step 5) was added to 190 μL of the competent cells. The ligation mixture with the competent cells was incubated on ice for 1 hour, then subjected to a heat shock at 42° C. for 90 seconds, and then again incubated on ice for 5 minutes. After that, 1 mL of LB broth was added and E. coli cells were grown at 37° C. and 250 rpm shaking for one hour.

The resulting transformed cells were plated into LB/amp/IPTG/Xgal plates. LB/amp/IPTG is Luria-Burtani Medium containing 1.5% agar, 75 μL/mL ampicillin, with each agar plate subsequently overlaid with 20 μL of a 100 mM solution of isopropyl-thio-beta-D-galactopyranoside in water and 50 μL of a 2% solution of 5-bromo-4-chloro-3-indolyl-beta-D-galactopyranoside in dimethyl sulfoxide. This agar medium is referred to as LB/amp/IPTG/Xgal. After that, E. coli colonies were screened to determine which colonies contained plasmids with the desired DNA insert. The screening is based on E. coli color change. E. coli that have been transformed with the plasmid that had the insert from a RT-PCR of step 3 and subsequent PCR of step 4 would be white. Those E. coli colonies that have been transformed with a plasmid that did not contain the desired insert would be blue. Several of the white colonies were tested to make sure that they did, in fact, contain the DNA insert in question.

7. Plasmid Preparation for Nucleotide Sequencing

To obtain the nucleotide sequence of the cocoon silk protein, plasmids-were first prepared for sequencing by selecting white colonies from the cells of step 6, growing them overnight, and then putting them through the Biorad plasmid mini-prep kit (Cat. No. 732-6100). Eag 1 (New England BioLabs, Cat. No. 505S) was preferably used as the restriction enzyme to digest the plasmid to screen for an insert approximately 600–700 bp in length.

8. Nucleotide Sequence

T7 and SP6 primers were preferably used to sequence the insert of step 7. These primers were provided by the sequencing facility. Sequences for the above primers are as follows:

```
Primer #3, T7 primer:
5' TAA TACGA CTCAC TATAG GGCG A 3'        SEQ ID NO: 4

Primer #4, SP6 primer:
5' AT TTAGG TGACA CTATA GAATA C 3'        SEQ ID NO: 5

The following nucleotide sequence of the insert
of step 7 was derived:
5' end
                                          SEQ ID NO: 6
                                          AG CTC TCC

CAT ATG GTC GAC CTG CAG GCG GCC GCA CTA GTG ATT

GGA GTT GCT CCA AAG AAG TAC CGC AAG GGA CAC TAT

GTC GGG GGT TAC GGG AAG AAG TAT CGT ATT TTT GAC

AGC AAT TGT GCT ATG AAC AAC GCC AAC TGT CAG AAT

CCA AAC GAA TCC GCC TTC GCC GAA GTT GAT TTC ACG

CTG TGC AAT GAT ATC AAA TGT CCT AGG AAA TGC GAT

AAA AAA CTA GAC CCG GTT TGT GCT TTT GAT GGG AAA

ACG TAC AGA CAA TTT AAC AAC AAA TGT CTG CTG CAA

GAA TTC AAT GAT TGC GAT CAA AAT GTG TTT CAA TAT

TTC AAC GCT GTG ACT AAC AAA AAA ATG TGC GTG GTT

GAG AAG CCA AAA TGC CCG ACC ATT TGT CCA GCA ATT
```

-continued

```
TAT GCT CCC GTT TGT GGT CGA AAT GCC AAA GGG GAT

TAC AAA AGT TTT GCG AGT GAA TGC AAC CAA TCC GCA

TTC AAC TGC TTG ATT TCT AAG AAT CAA TAT ACG GGC

AAG TAT GAT TTG AGT TTT TGC GAC ATC GAG TTC CCT

TAA GCA TGA CGT TGT AAC GTT TTT TCT CTG GAT GTG

CAA AAC ATA AAT TAC AAG CAC TGG ATT GAA TGG TGT

TTT ATT AAA TTT CCT TGT GAC CTT TTT TCC ATT ATT

CTT TCC GGC TTA CAA GTA ATC AAT ATT GAT ATC

GGT CGT TTT TGT AAA GAT TTT TTT TCA GTA AAA ATA

TCC ATC TCA TTT TCA CAA AAA AAA AAA AAA AAA

AAA AAA AAA AAG CTT GTA CAA AAA ATC CCG CGG CCA

TGG CGG CCG GGA GCA TGC GAC GTC GGG CCC A
```

The underlined section of the above sequence corresponds to the deduced reading frame of the black fly cocoon silk protein gene. In general, the deduced reading frame is the codon sequence that is determined by reading nucleotides in groups of three, starting from a specific start codon. In this case, the initial amino acid sequence was determined from N-terminal portion of the protein and this sequence then corresponded to the nucleotide sequence when read in triplets (codons).

9. Complete Amino Acid Sequence for Cocoon Silk Protein (Deduced from Nucleotide Sequence)

The DNA sequence of step 8 (SEQ ID NO: 6) was assessed for stop codons and the encoded amino acid sequence was deduced using all of the underlined nucleotides as shown in SEQ ID No: 6. The amino acid sequence was deduced to be as follows:

```
GVAPKKYRKGHYVGGYGKKYRIFDSNCAMNNANCQNPNESAFAEVDFTLCNDIKCPR    SEQ ID NO: 7
KCDKKLDPVCAFDGKTYRQFNNKCLLQEFNDCDQNVFQYFNAVTNKKMCVVEKPKCP
TICPAIYAPVCGRNAKGDYKSFASECNQSAFNCLNSKNQYTGKYDLSFCDIEFP
```

Due to the redundancy of the genetic code, i.e. more than one nucleotide triplet (codon) can code for a single amino acid, more than one nucleotide sequence can potentially code for cocoon silk protein. Therefore, various other homologues can code for cocoon silk protein. Homology refers to sequence similarity between two peptides or between two nucleic acid molecules. Homology is determined by comparing a position in each sequence which may be aligned for purposes of comparison. When a position in the compared sequence is occupied by the same base or amino acid, then the molecules are homologous at that position.

Although the invention has been described with reference to certain specific embodiments, various modifications thereof will be apparent to those skilled in the art without departing from the spirit and scope of the invention as outlined in the claims appended hereto.

The emodiments of the invention in which an exclusive property or privilege is claimed are defined as follows:

1. An isolated polypeptide molecule having an amino acid sequence of SEQ ID NO: 1.
2. An isolated polypeptide molecule having an amino acid sequence of SEQ ID NO:7.
3. A fiber formed from the polypeptide of claim 2.
4. A fiber formed from the polypeptide of claim 1.

* * * * *